United States Patent
Kreischer et al.

(10) Patent No.: US 8,778,120 B2
(45) Date of Patent: Jul. 15, 2014

(54) TRANSMISSION LASER WELDING METHOD FOR CONNECTING SHAPED PLASTIC BODIES

(75) Inventors: Thomas Kreischer, Saarbrucken (DE); Franz Kugelmann, St. Wendel/Bliesen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 867 days.

(21) Appl. No.: 12/295,990

(22) PCT Filed: Apr. 5, 2007

(86) PCT No.: PCT/EP2007/003127
§ 371 (c)(1),
(2), (4) Date: May 8, 2009

(87) PCT Pub. No.: WO2007/115803
PCT Pub. Date: Oct. 18, 2007

(65) Prior Publication Data
US 2009/0218325 A1  Sep. 3, 2009

(30) Foreign Application Priority Data
Apr. 6, 2006 (DE) .......................... 10 2006 016 299

(51) Int. Cl.
*B29C 65/16* (2006.01)

(52) U.S. Cl.
USPC .................................... 156/272.8; 156/380.9

(58) Field of Classification Search
USPC ........... 156/272.8, 308.4, 272.2, 379.6, 380.9
See application file for complete search history.

(56) References Cited

U.S. PATENT DOCUMENTS 3,769,117 A * 10/1973 Bowen et al. ................... 156/69
3,957,339 A *  5/1976 Engel ........................ 359/198.1
(Continued)

FOREIGN PATENT DOCUMENTS

DE   10 2005 010193 A1   9/2006
EP      0 087 403 A      8/1983
(Continued)

OTHER PUBLICATIONS

International Search Report dated Sep. 6, 2007 for International Patent Application No. PCT/EP2007/003127 filed on Apr. 5, 2007.

(Continued)

*Primary Examiner* — Richard Crispino
*Assistant Examiner* — Elizabeth Royston
(74) *Attorney, Agent, or Firm* — Millen, White, Zelano & Branigan, P.C.

(57) ABSTRACT

The present invention relates to an apparatus for welding tube segments to a tubular shaped body, and to a laser welding method for connecting a tube segment to a tubular shaped body, in which the tube wall of the tube segment is constructed from at least two material layers that differ from each other, and one of these layers contains, at least portionally, an absorber for laser radiation, comprising the steps of provision of a PVC-free tube segment and a tubular shaped body, positive insertion of tube segment and tubular shaped body into one another with the result that surface regions of the tube segment and of the tubular shaped body overlap, irradiation of the overlapping surface regions with laser radiation of defined wavelength, wherein it is unnecessary, in the case of the laser welding method, to move either the joint partners or parts of the apparatus.

14 Claims, 4 Drawing Sheets

(56) References Cited

U.S. PATENT DOCUMENTS

| | | | |
|---|---|---|---|
| 5,115,761 A * | 5/1992 | Hood | 118/641 |
| 6,749,933 B2 * | 6/2004 | Dries et al. | 428/328 |
| 6,752,826 B2 * | 6/2004 | Holloway et al. | 623/1.13 |
| 8,100,161 B2 * | 1/2012 | Caldwell et al. | 156/380.9 |
| 8,343,299 B2 * | 1/2013 | Caldwell et al. | 156/272.8 |
| 2004/0035524 A1 * | 2/2004 | Link | 156/272.8 |
| 2005/0000641 A1 * | 1/2005 | Hartmann et al. | 156/272.8 |
| 2005/0167407 A1 | 8/2005 | Chen et al. | |
| 2006/0086701 A1 | 4/2006 | Perreault et al. | |
| 2006/0264897 A1 * | 11/2006 | Lobl et al. | 604/506 |

FOREIGN PATENT DOCUMENTS

| | | |
|---|---|---|
| EP | 1 518 664 A | 3/2005 |
| EP | 1 609 555 A | 12/2005 |
| FR | 2 597 379 A1 | 10/1987 |
| FR | 2 812 372 A1 | 2/2002 |
| JP | 01 151464 A | 6/1989 |
| JP | 2005-104132 | 9/2003 |
| JP | 2005-305985 A | 5/2004 |
| JP | 2009 503497 | 1/2009 |
| WO | WO 2005/097471 A * | 10/2005 |
| WO | WO 2005/113049 A | 12/2005 |

OTHER PUBLICATIONS

English Translation of JP Patent Application No. 2009-503497.
English Translation of the Abstract of JP2005104132.
English Abstract of German Application No. DE102005010193A1; Title: "Connection of plastic pipes, comprises positioning the primary pipe relative to the secondary pipe, and then irradiating the connection region using infra-red radiation"; Applicant: REHAU AG Co.; Inventor: Hermann Andreas et al. Publication Date: Sep. 7, 2006. Thomson Innovation Record View (pp. 8).

* cited by examiner

TRANSMISSION LASER WELDING METHOD FOR CONNECTING SHAPED PLASTIC BODIES

The present invention relates to a transmission laser welding method for welding, in particular, tube sections made of plastic to substantially tubular shaped bodies, such as further tube segments, connectors, fittings, closures, etc.

In principle, various possibilities exist for positively connecting shaped bodies made of plastic, in particular of differing plastics. For example, the two shaped bodies can be connected positively to each other by means of adhesive bonding or welding methods.

Of the welding methods, in addition to IR welding (see, for example, WO 2005/080067) welding by means of laser radiation has recently been examined particularly intensively.

The fundamental physical principle of a welding method by means of laser requires that at least a portion of the applied laser light be absorbed by the material of at least one of the two shaped parts to be connected to each other, at least to such an extent that it can be converted into heat and the material at the site heated by the laser light becomes fluid through heating and renders possible a positive connection to the plastic material of the second shaped part.

Parameters limiting the welding method are the wavelength of the laser light used and the absorption behaviour of the plastic at this wavelength. In particular, in this case high-power diode lasers having a wavelength of 610-840 nanometers and Nd:YAG solid-state lasers having a wavelength of approximately 1,050 nanometers are used either in the visible light range (400-750 nanometers) or in the infrared range. Frequently, however, it is also possible to use $CO_2$ gas lasers having a wavelength of approximately 11,000 nanometers.

The absorption characteristics, and therefore the processing, of plastics differ greatly in dependence on the laser radiation wavelength used. Inhomogeneities in the plastic, such as, for example, pigments, fillers or reinforcing materials, but also crystalline superstructures in the case of partially crystallizing plastics, scatter the input radiation and reduce in particular the depth of penetration of the radiation into the plastic.

When a laser beam is incident upon a plastic part to be heated, the laser radiation is reflected, absorbed and transmitted to differing extents. The decrease in intensity of the radiation penetrating into the plastic can be described, in dependence on the material depth, according to the so-termed Bouguer's law. In this case, the input intensity decreases exponentially with the material depth.

Problems occur particularly as a result of the thermal decomposition resulting from radiation heating of plastics, in particular by means of $CO_2$ lasers. This has to do with the poor thermal conductivity of plastics, since the surface temperature of the plastic part often increases rapidly, wherein there is the risk of thermal material decomposition. [The principles of laser welding methods are described, for example, in H. Potente et al. "Laserschweißen von Thermoplasten" (Plastverarteiter 1995, No. 9, page 42 ff.), F. Becker et al. "Trends bei Serienschweißverfahren in *Kunststoffe* 87 (1997, page 11 ff.) and by H. Puetz et al in *Modern Plastics* (1997, page 121 ff.)].

The absorption behaviour, and therefore also the transmission, of a polymer or plastic that is laser-transparent at a certain wavelength can be controlled, for example, through the admixing of absorbers. Such absorbers are, for example, carbon black or, also, special dyes that have been developed in recent years.

A series of dyes that render possible such a controllable absorption behaviour are commercially available, and have been specially developed to be admixed in polymer mixtures in order to render possible laser welding at defined wavelengths. Also available for this purpose are the dyes disclosed by I. A. Jones et al. in "Use of infrared dyes for Transmission Laser Welding of Plastics" (Tech 2000 Conference Proceedings, page 1166 ff.).

A special form of the laser welding method, namely, laser transmission welding methods, also have the advantage, in comparison with other welding methods, that even complex geometries of the joint surface can be welded rapidly and efficiently. In the case of tube pieces being welded to, for example, connectors, fittings, etc., it is necessary for one joint partner to be irradiated all the way through by the laser beam, i.e. for laser radiation not to be absorbed. The second joint partner or parts of the second joint partner must be capable of absorbing the laser light with the generation of heat. The irradiation is usually effected from the outside of a joint partner.

EP 1552916 A1 describes, for example, the connecting of tubular shaped bodies by means of laser welding methods, wherein, however, it is necessary for the laser to be rotated around the connection joining the shaped bodies, wherein this requires complex apparatus and mechanisms, in order that two three-dimensional parts can be welded to each other in a joinless manner.

US 2003/0141634 describes laser-weldable tubes for medical applications, wherein, in a tube having a multilayer structure, each layer comprises a laser-absorbing material. Here, likewise, it is necessary for either the tube or the entire laser transmission apparatus to be subjected to a rotary movement, in order that the tubes can be welded to each other over their entire circumference.

DE 10245355 A1 describes the connection of a tube element via a sleeve. In a so-termed laser transmission method, a tube portion, a so-termed connector and the sleeve are welded to each other. In this case, likewise, the welding necessitates a weld seam that is continuous around the entire circumference, which is effected only through rotating the laser device or the tube to be welded.

WO 2005/063469 discloses tube pieces that can be connected to each other via so-termed sleeves. The connection between tube and sleeve is effected via a connection material, which contains a material that is absorbent at 700 to 2500 nm. In this case, the laser welding operation necessitates a rotational movement of either the laser or the tube being welded.

In the case of this laser welding method known from the prior art, it is thus disadvantageous, in particular, that the joint surfaces between the two shaped parts to be connected together have to be irradiated all the way round by the laser. This requires that the surfaces that are to be connected to one another be accessible to the laser from all sides. Frequently, the geometry of certain components does not permit all-round irradiation. Frequently, it has not been possible to effect rotation of the respective component because of its geometry, with the result that, in many cases, laser welding has not been possible hitherto.

It has therefore been an object of the present invention to provide a laser transmission welding method that remedies the above-mentioned disadvantages of the prior art and, in particular, makes it possible for a complete, all-round welding of two shaped parts that are to be connected to each other to be rendered possible without rotation. It is further an object of the present invention to provide an apparatus by means of which two shaped parts that are to be connected to each other can be welded rapidly, without the need to rotate a part of the apparatus or one of the parts to be welded.

According to the invention, the object is achieved by an apparatus for welding two joint partners consisting of a tube segment and a tubular shaped body, which apparatus comprises a laser and a mirror, wherein the laser, the joint partners and the mirror can be arranged such that the beam of the laser is incident upon the joint partners and then upon the mirror, wherein the mirror has partially the contour of the inner surface of a hollow cylinder. With the aid of this apparatus, the layer containing the absorber can be irradiated more uniformly. Overheating of localized regions of the tube does not occur, and the weld seam becomes more homogeneous.

In a preferred embodiment, the beam of the laser is divergent in a beam portion, and the divergent beam portion is first incident upon the tube segment and then upon the mirror. An advantage of this embodiment is a yet more uniform irradiation of the layer containing the absorber.

Usually, the joint partners that are to be connected, being the tube segment and the tubular shaped body, are irradiated by means of a laser beam. On the one hand, a major part of the provided laser energy is lost during welding, owing to scattering and reflection effects. All rays that are not vertically incident upon the tube surface are deflected, beyond a certain limiting angle the beams undergo total reflection and are not instrumental in the welding of the joint partners. Further, the laser-absorbing layer of material that is to be penetrated is substantially greater in the edge regions, and is therefore also instrumental in less energy being supplied to the regions underneath. Through the reflection of the beams on the mirror, energy that would otherwise be lost as a result of reflection or transmission is utilized. The beams reflected on the mirror can re-enter the tube material so as to be available for a welding operation.

The contour of the mirror describes a portion of an inner surface of a hollow cylinder. The opening on one side, which is absent from the fully cylindrical contour, serves as an aperture for the incident laser beam. Slight variations on the ideal contour of a hollow cylinder are possible. The cross-section of the hollow cylinder would then not be circular, but elliptical.

In the scope of this invention, a laser beam is divergent if the beam cross-section becomes greater in the beam direction. The advantage of this arrangement is that, in the case of the apparatus being used for a welding operation, all regions of the layer of a tube segment that comprises the absorber can be irradiated uniformly. Temperature differences within the layer comprising the absorber are thereby kept small.

The mirror is preferably composed of aluminium or an aluminium alloy. It has been found that, in particular, mirrors made of polished aluminium has the best reflection characteristics. Mirrors made of steel heat up to a very great extent and reflect imperceptibly. Mirrors made of brass also heat up, but also reflect a portion of the radiation. The reflection effect decreases as the mirror surface becomes increasingly dulled, which is the result of heating. However, a surface can be restored to good reflection by repolishing.

The diameter of the hollow cylinder is preferably between 5 and 25 mm, yet more preferably 20 mm. The distance between the mirror surface and the surface of the joint partners should not be too great, in order that too much of the light energy reflected on the mirror is not radiated without penetrating the joint partners. Further, preferably tubes having a total diameter of up to 13 mm can be welded by means of this apparatus. Tubes having a greater diameter usually have greater wall thicknesses. In particular, the layer containing no absorbers is thicker. This layer has a greater heat absorption capacity. With this greater heat absorption, heat is removed from the welding process, with the result, rather, that weld seam defects can occur. Tube size and distance between mirror surface and surface of the joint partners are the limiting factors in respect of the diameter of the hollow cylinder.

Preferably, a diode laser having a wavelength of from 750 to 1000 nm, more preferably 808 nm, is used in the case of the apparatus according to the invention. The laser can have a power of between 380 and 520 W, more preferably a power of 500 W. By means of the diode lasers, it is possible to produce laser beams that can converge and diverge. The lasers in this case are so-termed "fanned-out diode array lasers". Further, the power of the laser and the wavelength of the light emitted by the laser are optimum for the welding process, with the result that no weld seam defects are produced and the polymer material does not become overheated.

The object on which the invention is based is further achieved in that there is provided a laser welding method for connecting a PVC-free tube segment to a tubular shaped body ("the joint partners") through the use of a laser and a mirror, wherein the tube wall of the tube segment is constructed from at least two material layers that differ from each other, and one of these layers contains, at least portionally, an absorber for laser radiation, wherein, in the method a) the PVC-free tube segment and the tubular shaped body are provided,
b) the tube segment and the tubular shaped body are inserted positively into one another with the result that surface regions of the tube segment and of the tubular shaped body overlap,
c) the tube segment and the tubular shaped body are arranged, with overlapping surface regions, in front of the mirror,
d) the tube segment and the tubular shaped body, with the overlapping surface regions, are irradiated with laser radiation, with the result that the laser beams reflected or transmitted from the tube segment or from the tubular shaped body are reflected by the mirror and are again partially incident upon the tube segment or the tubular shaped body, wherein a weld connection is realized between the tube segment and the tubular shaped body.

By means of this method, the duration of irradiation can be reduced substantially in comparison with welding methods in which it is necessary to move joint partners to be welded or parts of the apparatus. The laser light radiated at the joint partners through reflection and transmission is reflected on the mirror and is available again for a further welding operation, with the result that the laser and/or the joint partners to be welded need not be moved. The duration of irradiation is therefore reduced to a few seconds. Preferably, the joint partners can be welded to one another in less than 3 seconds. In the case of the method, therefore, irradiation is effected in step d) for not more than 3 seconds.

In order to achieve optimum results and to form a homogeneous weld seam, in the method use is made of a mirror, which has the contour of the inner surface of a hollow cylinder. Yet more preferably, the method is performed with use of the apparatus according to the invention.

In the case of a preferred embodiment of this method, the diameter of the laser beam, when incident upon the tube portion, is less than the diameter of the tube portion to be welded. The ratio of the diameter of the laser beam to the diameter of the tube portion is preferably between 1 to 2 and 1 to 5.

The method according to the invention dispenses with all travel paths, since the radiation is radiated uniformly onto the entire surface with the aid of the mirror. All travel paths are also dispensed with if the diameter of the beam portion, when incident upon the tube portion, is less than the diameter of the tube portion.

A further advantage of the method according to the invention consists in that a more uniform welding pattern is achieved. To be regarded as a positive secondary effect is the space obtained between the laser optics and the welding site, as a result of which the joint partners can be more easily inserted in and removed from the mount.

If a mirror is used that has the contour of the inner surface of a hollow cylinder, the distance between the mirror and the tube wall is approximately equal all the way round. If the mirror of the apparatus does not describe exactly the contour of a hollow cylinder, the distance between the mirror and the tube wall can be unequal. If the cross-section of the hollow cylinder is elliptical, the joint partners to be connected are arranged in a centred manner in front of the mirror.

The object on which the invention is based is further achieved in that there is provided a method for laser transmission welding for connecting a PVC-free tube segment to a tubular shaped body ("the joint partners"), wherein the tube wall of the tube segment is constructed from at least two material layers that differ from each other, and one of these layers contains, at least portionally, an absorber for laser radiation, comprising the steps of:

a) provision of the preferably PVC-free tube segment and the tubular shaped body,
b) positive insertion of the tube segment and tubular shaped body into one another with the result that surface regions of the tube segment and of the tubular shaped body overlap,
c) irradiation of a first, substantially semi-cylindrical segment of the overlapping surface regions with laser radiation of a defined wavelength,
d) attenuation of the laser radiation to 90-50% of the original energy through absorption in the layer containing the absorber, with a weld connection being realized in the first segment,
e) incidence of the attenuated laser radiation upon a second, substantially semi-cylindrical segment of the overlapping surface region that is arranged opposite a source for radiation and is substantially mirror-symmetrical in relation to the first segment, for the purpose of realizing a weld connection in the second segment.

Both methods according to the invention, whether with or without the use of a mirror, offer the advantage that the two joint partners are irradiated through from a single side only, wherein a positive weld connection of the joint partners is obtained all the way round. As a result, the methods according to the invention can be performed without rotation in respect of either the laser apparatus or the joining partners, with the result that a far less complex mechanical apparatus is required for performing the method according to the invention than in the case of the methods known from the prior art, which thus constitutes a substantial simplification.

If the method is performed without the use of a mirror, it may be necessary for the laser or the joint partners to traverse a slide course in order to produce uniform weld seams. An advantage of the method with use of the apparatus according to the invention is that a more uniform irradiation of the joint partners is possible, and no parts of the apparatus, or the parts to be welded, need be moved.

A mirror, for reflecting the laser light directed onto the joint partners, can also be used in the case of this method comprising the steps a) to e). If a mirror is used, the method additionally comprises the steps of incidence of the attenuated laser radiation upon a mirror, reflecting of the laser beam and renewed incidence of the light beam upon the tube segment.

For the purpose of performing the methods according to the invention, it is in this case essential to the invention that a tube segment having a multilayer structure be provided, wherein it is necessary for an absorber for laser radiation to be contained in a layer.

In the present document, the term "positive" is understood to mean that the tube segment and the tubular shaped body overlap one another in a gapless or joinless manner. The tube segment in this case preferably exerts a contact pressure upon the tubular shaped body.

The term "tube segment" is understood to mean any portion of a tube of any length through which fluids can be passed. Since use as a medical tube can be anticipated, for example in haemodialysis systems, it is necessary for the tube to be, in particular, of a PVC-free design, since relatively recent studies have shown that the plasticizers used in PVC (polyvinyl chloride) are dissolved by the biological fluids passed through the tube and can cause health hazards in a human organism.

The weldability, or the stability, of the weld connection is determined, in particular, by the quantity of absorber, for the laser light used, in the layer containing the absorber. According to the invention, an outer surface of the tube, i.e. either its inside or its outside, comprises a functionalized, i.e. absorber-containing, thin layer. This layer is typically co-extruded with the second layer located beneath it. The layer thicknesses of the layer containing the absorber are in the range from 20 to 100 μm, with the result that they can still also be produced in the lower layer thickness range through co-extrusion.

The arrangement of the layer containing the absorber either as the surface constituting the tube interior or, in a different embodiment of the invention, as the surface constituting the tube exterior, renders possible, in particular, various geometrical arrangements of shaped parts to be welded to each other: for example, in a preferred embodiment of the invention, the tube can be inserted in the tubular shaped body, thus, for example, in a connector, with the result that in this case the outer layer must be functionalized with the absorber, i.e. the layer that comes into contact with the second joint part to be welded, being the connector.

In a further advantageous embodiment of the invention, the functionalized layer, i.e. the layer containing the absorber, constitutes the inside of the tube segment, with the result that a tubular shaped body can be inserted in the tube.

In further preferred developments of the invention, only the portion of the layer that overlaps with the region of the tubular shaped body to be welded contains the absorber. This is possible, clearly, in the case of the two geometric alternatives described above. In particular, the use of expensive dyes for absorption is thereby also rendered possible.

The concentration of the absorber in the layer containing the absorber is typically between 50 and 300 ppm, preferably 80-200 ppm, and is selected such that only approx. 10-50%, preferably 15-40%, of the laser light used is absorbed along the length of the penetration path to of the laser light by the absorber-containing layer of the first substantially semi-cylindrical segment, and can thus be used for the welding of the first part. It is understood, in this connection, that a person skilled in the art matches the type and quantity of the absorber to the type of laser used, or to its wavelength, in order to achieve the aforementioned values.

Advantageously, the layers of the tube segment that can be used according to the invention are composed of PVC-free materials, in particular the layer containing the absorber is composed of polyolefins such as, for example, polyethylene, polypropylene, polyisoprene, also styrene-olefin copolymers such as, for example, styrene-ethylene-butadiene-styrene block copolymers (SEBS), styrene-ethylene-propylene-styrene block copolymers (SEPS), styrene-isoprene-styrene copolymers (SIS), styrene-ethylene-butadiene copolymers (SEB), and mixtures thereof.

The at least one further, absorber-free layer has the function of imparting a certain mechanical stability, buckling resistance, etc., to the tube segment.

For this purpose, pure polyolefin materials, in particular, such as polypropylene, polyethylene, polyisoprene and mixtures thereof are particularly preferred as materials for this layer. In further preferred embodiments, clearly, styrene-ethylene-butadiene-styrene block copolymers (SEBS), styrene-ethylene-propylene-styrene block copolymers (SEPS), styrene-isoprene-styrene copolymers (SIS), styrene-ethylene-butadiene copolymers (SEB), and mixtures thereof can also be used, or used with the pure polyolefins.

In further embodiments of the invention, the tube segment used according to the invention has an inner diameter of a maximum of 8 mm and an outer maximum diameter of 12 mm. Preferred wall thicknesses of the tube segment are 2 mm, in further specific embodiments such as, for example, in the case of an intended use of the tube as a so-termed blood system tube, even to 1.5 mm.

In further advantageous embodiments, the tube can comprise yet further optional sequences of layers. It is of importance only that these further layers do not impair the laser welding process, with the result that these layers must be substantially laser-transparent.

Even complex requirements, in particular in respect of mechanical stability, buckling resistance, elasticity, etc. can thereby be taken adequately into account.

A so-called diode laser is preferably used in the scope of the method according to the invention. This diode laser has a wavelength of up to 1000 nm, preferably of from 750 to 900 nm, most preferably of 808 nm. Of particular importance in the performance of the method according to the invention is that there is obtained, with or without the application of pressure, a joint plane at which both joint partners overlap one another preferably in a joinless manner, with the result that the positive connection is maintained particularly easily by the fluid polymer heated by the laser, with the result that, according to the invention, a great diversity can be obtained in the design of the weld seam geometry. The geometry used most frequently in the joining of plastics by means of a laser, in particular by means of a diode laser, is the overlapping seam, which is also used by preference in the present case.

It is important, in this connection, that the multiplicity of possible laser types envisaged for use in the scope of the present invention (e.g. Nd:YAG lasers if the method is performed without the use of a mirror, or a diode laser for the method according to the invention, whether with or without the use of a mirror, etc.), which consequently also have differing wavelengths, do not mean any limitation in respect of the absorber substances, owing to the great energy density of the laser radiation. Because of the great energy density, it is not necessary to irradiate in the absorption maximum of the respective selected absorber substance. It suffices if irradiation is effected in a window of approximately ±100 nm around the maximum of the respective substance, with the result that a wide range of absorbers can be employed for use in the method according to the invention. Usually, a laser emitting light beams that are as far as possible parallel is used in the case of the method comprising the steps a) to e).

In the method according to the invention in which no mirror is used for reflecting the laser beams, it is particularly preferred that the attenuation of the laser radiation along the length of the penetration path of the laser light by the absorber-containing layer of the first substantially semi-cylindrical segment, owing to the absorber, is approx. 10-50%, preferably 15-40%. These ranges make it possible, even in the case of longer penetration paths at individual circle segments of the tube, for sufficient laser radiation to still reach the opposite circle segment of the pumping tube, with the result that firm welding is rendered possible there also.

If the method is used without the use of a mirror, the laser power, in the case of a diode laser, is usually approx. 400 watts. It is understood that these values are merely guides for the person skilled in the art in the selection of the appropriate laser. In the case of this method, likewise, the laser used can be a "fanned-out diode array laser" that has a power of approximately 400 watts and focuses the radiation onto a spot of approximately 10 mm diameter. Typical time periods for the action of the laser radiation are 1-10 s, preferably 2-8 s, very particularly preferably 3-7 s, depending on the tube thickness. Exemplary time periods for the realization of a firm weld connection are, in the case of a blood pumping tube having a diameter of approximately 12 mm, 7 seconds, and, in the case of a tube having a diameter of 6.5 mm, approximately 3 seconds.

The object of the present invention is further achieved by a laser-welded joining connection between a tube segment and a tubular shaped body, which joining connection is produced by the methods according to the invention, whether used with or without mirror. Laser-welded joining connections that can be produced without particularly great mechanical complexity can be employed, in particular, in the medical domain, in this case particularly in the conveying of physiological fluids, infusion solutions or blood.

In this case, there are special requirements for the tube pieces and connecting pieces that are to be welded, with the result that the choice of the corresponding polymers must be in compliance in respect of transparency in the visible wavelength range, heat sterilizing capability and biocompatibility, which are known, however, from the prior art mentioned above. The present invention therefore likewise comprises a tube system comprising a multiplicity of such laser-welded joining connections between a tube segment and a tubular shaped body, for example a connector or a further tube segment, for use, for example, in a haemodialysis circuit.

The invention is explained more fully in the following with reference to embodiment examples in the following figures, but without this being intended to be understood as a limitation of the concept of the invention.

There are shown in.

Figure 1:
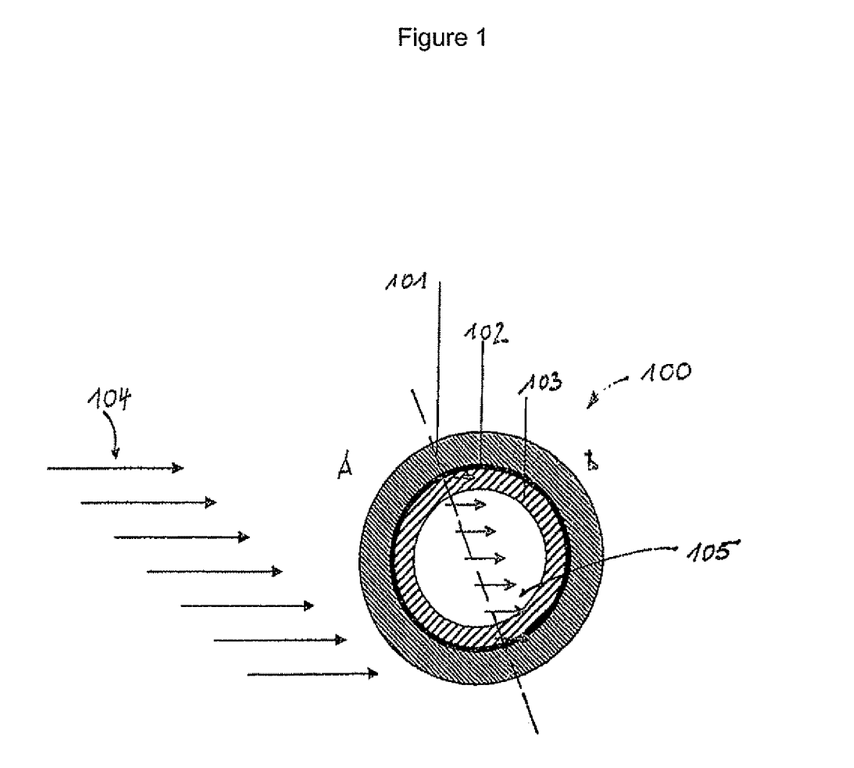
FIG. 1 a cross-section through a connection in which a connector has been pushed onto a tube segment.

FIG. 1 shows a combination 100, according to the invention, between a connector 101 made of polypropylene and a tube, which consists of an inner layer 103 and of an outer layer 102, the outer layer 102 containing a laser-absorbing material such as, for example, a dye. The layer 102 in this case has a thickness of approximately 50 μm. The absorber substance used can be, for example, Lumogen IR 788 by the company BASF, but it is also possible in the scope of the present invention to use any other optional absorber that absorbs in the wavelength range of the diode laser used. After the tube segment has been pushed into the connector 101, laser radiation 104 having a wavelength of 808 nm is applied over a period of 3-5 seconds. In a semi-cylindrical region denoted by the capital letter "A", the laser radiation 104 is absorbed by the absorber in the layer 102, and fuses the plastic, with the result that a positive connection is produced between the polypropylene connector 101 and the tube, at the outer layer 102. The radiation 104 is absorbed and, as explained in detail above, is incident, having been attenuated by approximately 10-50%, indicated by the arrows 105, into the second semi-circular segment B, where it is likewise absorbed by the absorber in the layer 102 and thereby produces a positive connection in segment B also by is fusing the layer 102 between the layer 102 of the tube segment and the polypropylene connector 101. The residual radiation is usually not fully absorbed. The figures also show the differing path lengths along which the wavefront of the laser light must pass: the path length $l_1$ in this case is much shorter than the path length $l_2$, with the result that light is attenuated less along the path length $l_1$, i.e. lies rather in the range of 10% attenuation, than along the path length $l_2$, where the absorption is rather at 50%.

Figure 2:
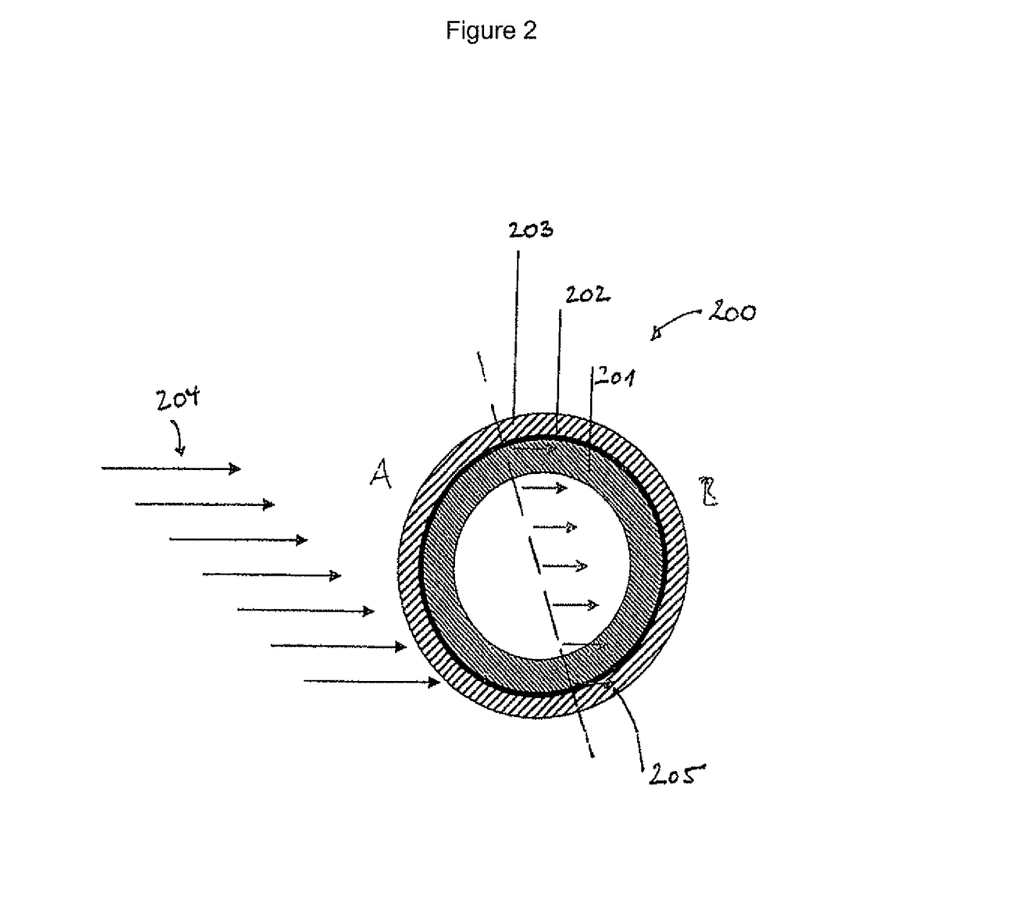
FIG. 2 a connection in which a connector has been pushed into a tube.

FIG. 2 shows a further embodiment of a connection 200, which can be used in the scope of the method according to the invention. In this case, a connector 201, for example made of polypropylene, is inserted in a tube segment, with the result that the inner surface of the tube 202 contains the laser-absorbing material and the outer layer 203 serves the purpose of stabilization.

It is understood that, clearly, yet further layers can be arranged on the outside or between the layers 202 and 200, provided that these layers are laser-transparent, as already mentioned above. The thickness of the layer 202 is likewise 50 µm, and Lumogen IR 788 by BASF has likewise been used as an absorbing substance.

The arrangement 200 is now likewise irradiated with laser radiation of a wavelength $\lambda=808$ nm (represented by arrow 204), which radiation is absorbed to approximately 10-50% in the first semicircle or semi-cylindrical segment A, with the result that a positive connection is produced between the surface of the connector 201 and the radiation-absorbing layer 202. The non-absorbed radiation 205 is incident upon the layer 202 in the semi-cylindrical segment B 202, where it likewise results in absorption, heating and fusing, with the result that full welding to the connector is achieved in the entire circumference of the tube segment.

With the method according to the invention, as has been shown here, rotation of the laser or of the joint elements 100 to 200 to be connected is therefore not necessary for the realization of an all-round weld seam.

Figure 3:
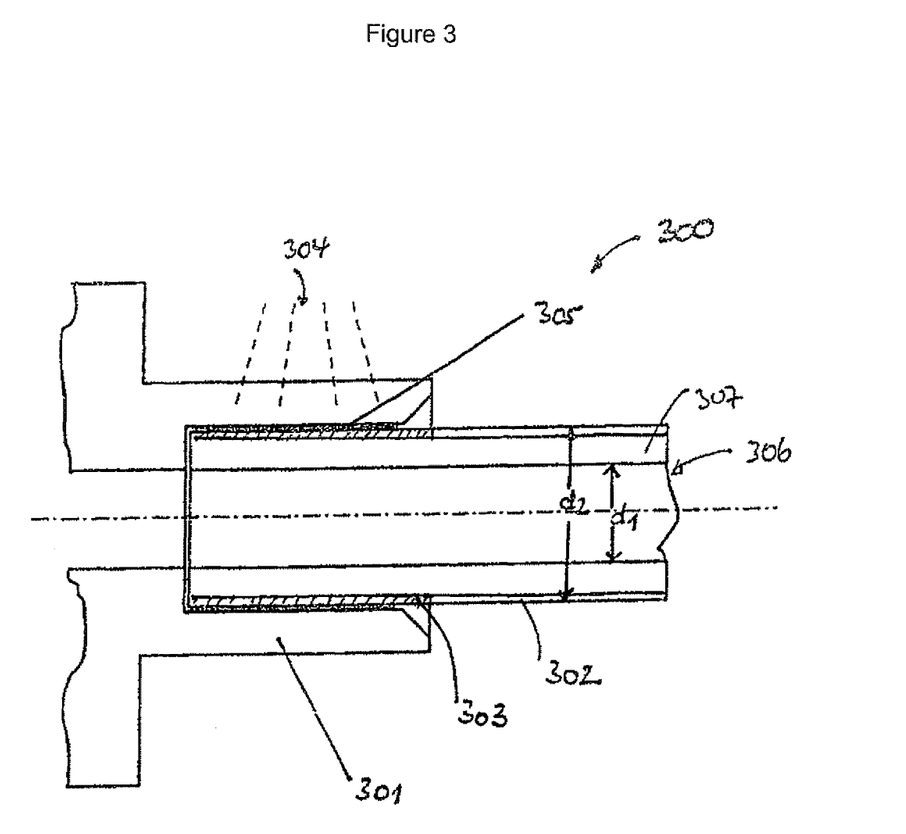
FIG. 3 a laser-welded joining connection between a connector and a tube inserted in the connector.

FIG. 3 shows a fully welded joining connection 300 between a connector 301, made of polypropylene, and a tube segment 306, which is of an inner layer 307, which has no laser-absorbing materials, and of an outer layer 302, which, in regions in the portion 303 that overlaps with the inside of the connector 301, contains an absorber for laser light. Following action of the laser radiation 304, a positive, all-round weld seam 305 is produced, as described in FIGS. 1 and 2.

Figure 4:
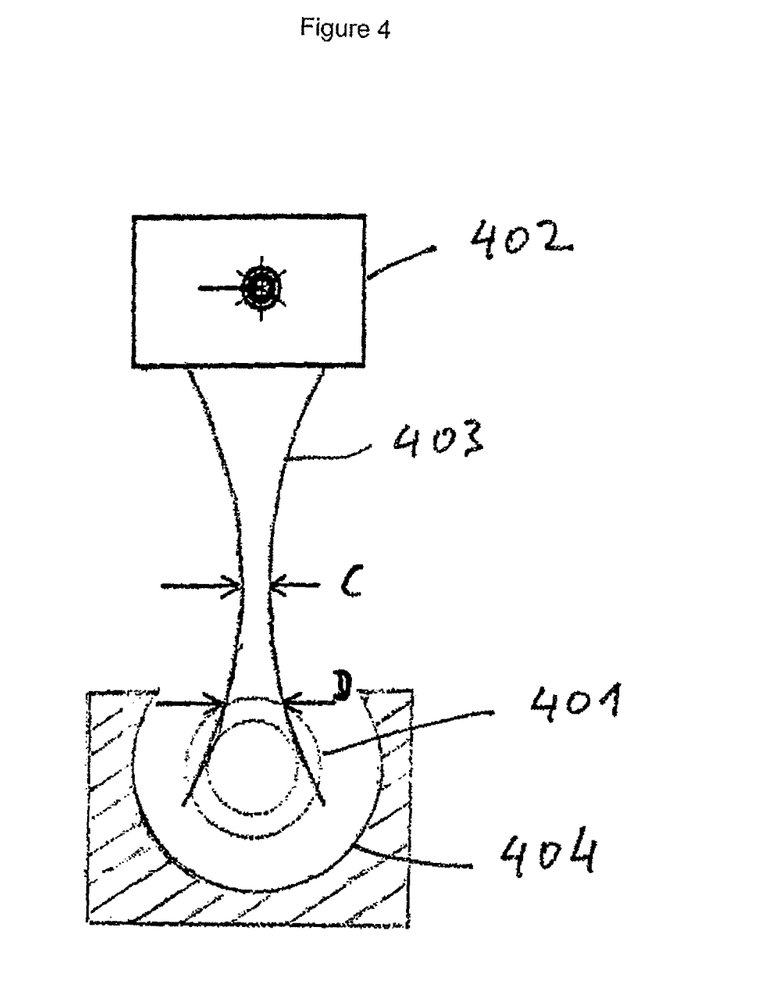
FIG. 4 an arrangement consisting of a laser and a hollow cylindrical mirror.

FIG. 4 shows an apparatus 400 for welding a tube segment 401, the apparatus consisting of a laser 402 and a mirror 404. The diode array laser emits a light beam 403, which converges in a first portion, has the least cross-section in the plane C, and then diverges. The divergent beam portion is incident upon the tube segment 401 in the plane D. Scattered and penetrating laser beams are then incident upon the mirror 404, where they are reflected, and are again partially incident upon the tube segment. By means of this arrangement, uniform irradiation of the layer comprising the absorber is ensured, with the result that the tube segment is welded uniformly.

Embodiment Example 1

In a preferred embodiment, a PVC-free tube having the following structure was used:

| | |
|---|---|
| Inner diameter | 8 mm |
| Outer diameter | 12 mm |
| Wall thickness | 2 mm |

The layer of the tube that contains the absorber has a composition as follows:

| | |
|---|---|
| Thickness of the absorber layer: | 50 µm |
| Composition: | 60% SEBS Tuftec 1221 (Asahi) |
| | 40% PP-R RD204 CF (Borealis) |
| | 100 ppm Lumogen IR 788 BASF |

The absorber-free layer was composed of a mixture of 70% SEBS Tuftec 1221 (Asahi) and 30% SIS (Hybrar 7125 F, Kuraray).

The tube segment having the two layers was produced by co-extrusion.

A so-termed connector, made of polypropylene, served as a second joint partner. In the embodiment example, the tube segment is pushed into the polypropylene connector in the manner described in FIG. 3, with the difference that the entire outer layer contained the absorber.

The joint partners inserted into one another, being the tube segment and the connector, were irradiated from a single side, according to the invention, by means of a diode laser made by the company Laserline, D-Mühlheim (diode laser LDF 1000-500), having a wavelength of 808 nm. So-termed transmission welding was used, with overlapping in the scope of the method according to the invention. A positive, all-round weld seam was thus obtained, according to the invention, without rotation of one or both joint partners.

The thus-obtained weld connection fulfils all requirements in respect of tightness of seal, tensile strength and heat sterilizing capability that are encountered in the medical domain. The tensile strength ("tube rupture strength") was determined according to DIN 53455 and was approximately 170 N. In the present case, the tube ruptured, whereas the welded connection did not loosen, even under the action of this force. Typically, the lower limit of the tensile strength of connections welded according to the invention was 120 N, and was a maximum of 160-170 N, depending on the area welded, wherein it is not possible—as stated above—to determine exactly a precise measurement of the upper limit, owing to the rupturing of the respective tube.

The invention claimed is:
1. A method for laser welding a PVC-free tube segment to a tubular shaped body through the use of a laser and a minor, said method comprising:
   a) providing a PVC-free tube segment and a tubular shaped body, wherein the tube wall of the tube segment is constructed from at least two material layers that differ from each other, and one of these layers contains, at least portionally, an absorber for laser radiation,
   b) positively inserting the tube segment and the tubular shaped body into one another with the result that the surface regions of the tube segment and of the tubular shaped body overlap, c) arranging the tube segment and the tubular shaped body, with the overlapping surface regions, in front of the minor, and d) irradiating the tube segment and the tubular shaped body, with the overlapping surface regions, with direct laser radiation from a single side only, with the result that the laser beams transmitted from the tube segment or from the tubular shaped body, as well as laser beams reflected by the tube segment or tubular body, are reflected by the mirror and are again partially incident upon the tube segment and/or the tubular shaped body, a weld connection being realized between the tube segment and the tubular shaped body, wherein said minor has the shape of the inner surface of a hollow cylinder, and said laser is a diode array laser, and said direct laser radiation is in the form of a laser beam that has a convergent portion and a divergent portion and the divergent portion irradiates said tube segment and said tubular shaped body.

2. The method according to claim 1, wherein the absorber is contained in the layer constituting the inner surface of the tube segment.

3. The method according to claim 2, wherein, in positively inserting the tube segment and tubular shaped body into one another, the tubular shaped body is pushed into the tube segment.

4. The method according to claim 1, wherein the absorber is contained in the layer constituting the outer surface of the tube segment.

5. The method according to claim 4, wherein, in positively inserting the tube segment and tubular shaped body into one another, the tube segment is pushed into the tubular shaped body.

6. The method according to claim 1, wherein the absorber is contained in the absorber-containing layer at a concentration of 50-300 ppm.

7. The method according to claim 6, wherein the layer containing the absorber is composed of a PVC-free material.

8. The method according to claim 7, wherein the material is selected from polyethylene, polypropylene, polyisoprene, styrene-olefin block copolymers such as SEBS, SEPS, SIS, SEB and mixtures thereof.

9. The method according to claim 6, wherein the layer thickness of the layer containing the absorber is 20 to 100 μm.

10. The method according to claim 1, wherein the material of the absorber-free layer is selected from polyethylene, polypropylene, polyisoprene, styrene-ethylene-butadiene-styrene block copolymers (SEBS), styrene-ethylene-propylene-styrene block copolymers (SEPS), styrene-isoprene-styrene copolymers (SIS), styrene-ethylene-butadiene copolymers (SEB) and mixtures thereof.

11. The method according to claim 1, wherein the tube segment has a wall thickness of a maximum of 4 mm.

12. The method according to claim 1, wherein the tubular shaped body is a connector or a further tube segment.

13. The method according to claim 12, wherein the connector is composed substantially of polypropylene.

14. The method according to claim 1, wherein the method can be performed without the need for rotating the laser, the PVC-free tube segment, or the tubular shaped body.

* * * * *

UNITED STATES PATENT AND TRADEMARK OFFICE
CERTIFICATE OF CORRECTION

| | | |
|---|---|---|
| PATENT NO. | : 8,778,120 B2 | Page 1 of 1 |
| APPLICATION NO. | : 12/295990 | |
| DATED | : July 15, 2014 | |
| INVENTOR(S) | : Thomas Kreischer et al. | |

It is certified that error appears in the above-identified patent and that said Letters Patent is hereby corrected as shown below:

In the Claims

Column 10, line 57 reads, "a tubular shaped body through the use of a laser and a minor,", should read --a tubular shaped body through the use of a laser and a mirror,--;

Column 11, line 3 reads, "minor, and", should read --mirror, and--;

Column 11, line 15 reads, "wherein said minor has the shape of the inner surface of a", should read --wherein said mirror has the shape of the inner surface of a--.

Signed and Sealed this
Twenty-first Day of April, 2015

Michelle K. Lee
*Director of the United States Patent and Trademark Office*